Jan. 15, 1935. E. G. WILKINSON Plant Pat. 119
MANGO
Filed Aug. 21, 1933
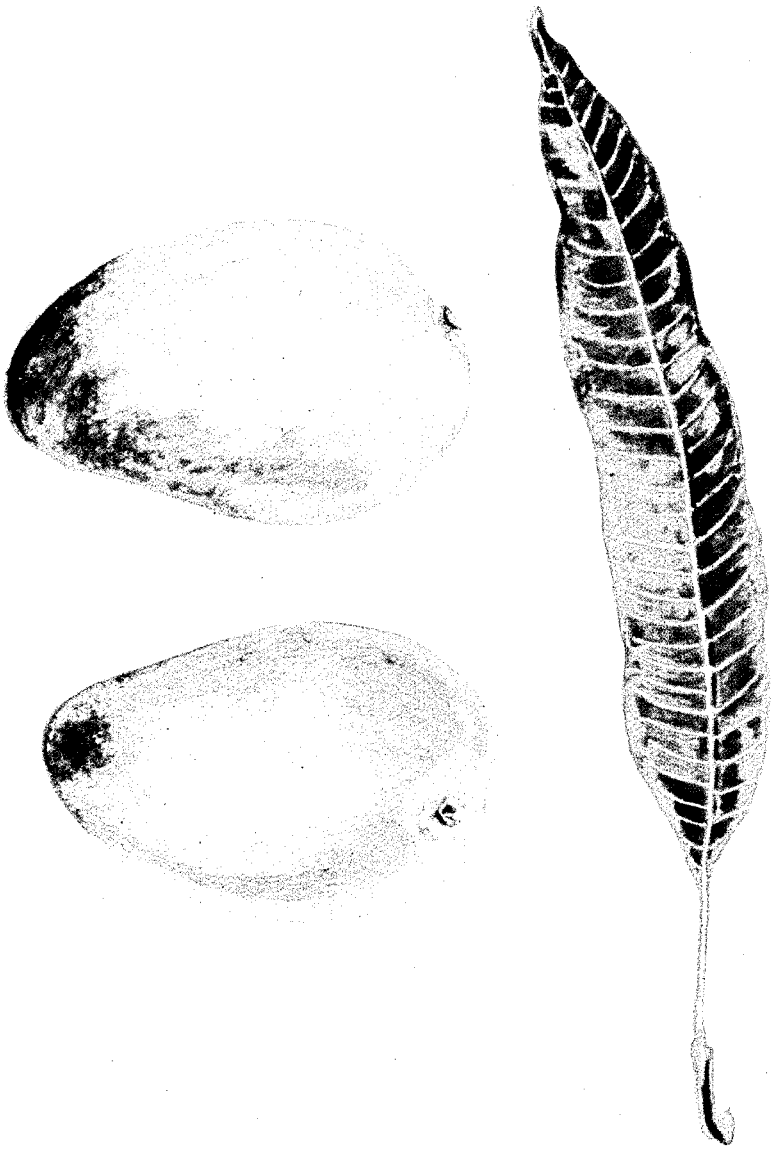
Inventor
Edwards G. Wilkinson
By James J. Sheehy & Co.
Attorneys Patented Jan. 15, 1935

Plant Pat. 119

UNITED STATES PATENT OFFICE

119

MANGO

Edwards G. Wilkinson, Naples, Fla.

Application August 21, 1933, Serial No. 686,129

1 Claim. (Cl. 47—62)

My invention relates to a new variety of mango.

The principal object of my invention is to produce a mango that is of better eating qualities than any mango which has as yet been found on the market.

The annexed painting and the following description set forth the leading characteristics of the new variety of mango which I have asexually produced.

The variety of the subject of this application was originated on applicant's home grounds, Naples, Florida, and the first fruit ripened in 1932. The variety originated from a seedling, the seed however was selected from trees where the branches were intertwined and is the result of many years of experimentation to produce a better mango that would be of value commercially, the purpose being to secure a seed that had been cross fertilized and in this way getting a hybrid.

The parentage is not positively known as to both parents, one is certainly "Cecil" the other is either Mulgoba or Haden, applicant is of the belief that it is Mulgoba.

This variety was first asexually propagated by budding in the spring of 1933. The buds (12 in number) have reproduced the leaf, form, color of young growth, and odor of the leaf; these buds reproduced the fruit in the summer of 1934.

*Tree*

The tree is low growing and wide spreading, of an extraordinary vigorous growth and while it is not symmetrical it has a tendency to horizontal growing, this being very noticeable before the trees begin to bear. The tree sets fruit on every bloom flush and will hold and ripen more fruit than the limbs will carry, which makes it necessary to support at least half of the limbs. The new growth is of a greenish hue rather than the usual reddish bronze.

*Leaves*

The leaves are of large size and are noticeably very sharp pointed with twenty-five to thirty transverse veins. When crushed the leaves give off a fresh herby odor and are a fern to a wintergreen in color.

*Pannicles*

The pannicles are of all sizes, from as large as a man's thumb to heads 24" high to 34" across with as many as seven heavy stems, in other words, from a bunch of a few flowers on a perfectly foliaged piece of new growth to 25—6" to 8" pannicles along an 18" stem with a leaf at each pannicle. Most of the pannicles are very large causing bending down of heavy branches with their weight, making it necessary to stake up the branches to keep the bloom off the ground. Since a large proportion of the pannicles hang downward bloom drainage is good. The color of the pannicles is usually red but sometimes they are of a light green and are larger in size than any known mango. The flowers are abundant and the percentage of perfect flowers is very high.

*Color*

The blushed portions of my mango have a greater area of bright color of scarlet vermilion than those of the Mulgoba or of any other known variety (see Maerz & Paul Dictionary of Color). The green portions are brighter and more yellowish green than those of the Mulgoba and are smaller in area. The apex of the fruit is of a fern green shade and the skin shows an orange reddish coloring and portions being a golden-rod yellow while the Haden variety of mango is of the apricot yellow.

*Fruit*

The fruit is large to very large and from 14 to 28 ounces in weight. The general shape appears to resemble the Mulgoba variety but many specimens appear to lack its level depressed stem portion, thus in this respect somewhat resembling the Haden variety. Endwise it appears round; it is full shouldered, plump, long and the lower half tapering. Its skin is thinner than any known variety, strong and of a spicy odor, many persons preferring to eat them unpeeled. The flesh of the fruit is yellow, not orange as in the known varieties of mango; is free from fibre and of a delicious mild spicy flavor, hence does not require an acquired taste to enjoy it. The flesh holds firm and does not deteriorate for a long time, even after the skin has turned entirely black and even this blackened peel will be no thicker than the stringy lined peel of the Haden variety when first ripe. The fruit is approximately $11\frac{1}{16}$ inches in length and is $7\frac{1}{8}$ inches in diameter.

*Seed*

The seed is oblong, narrow and flat and a few show fibres along the ventral edge only. The large size of the fruit combined with the lack of fibre on the sides and back of seed makes it a superior slicing mango. The seeds are 95% monoembryonic.

The extreme limits of fruiting, so far, have been May 15 to August 15. The first crop is the most abundant and fruits the last week in May and the first week in June. The second crop is at its best during the latter half of July.

In order to differentiate my mango from any other known variety, I wish to state in conclusion:—

First;—that it is of brighter colors being a deeper scarlet vermilion, brighter yellow and brighter green, making it commercially of more value, as attracting by its color.

Second;—its tree has a greater bearing capacity—a multiplicity of crops.

Third;—has greater keeping qualities, hence stands shipment better.

Fourth;—a more pleasing flavor and a delicious fragrance.

Fifth;—its greater size.

What I claim is:—

A new and distinct variety of mango tree, as described, characterized particularly by its low and vigorous growing habits; multiplicity of its crops; superior size, color, flavor and freedom from fibre of its fruit.

EDWARDS G. WILKINSON.